Figure 1:
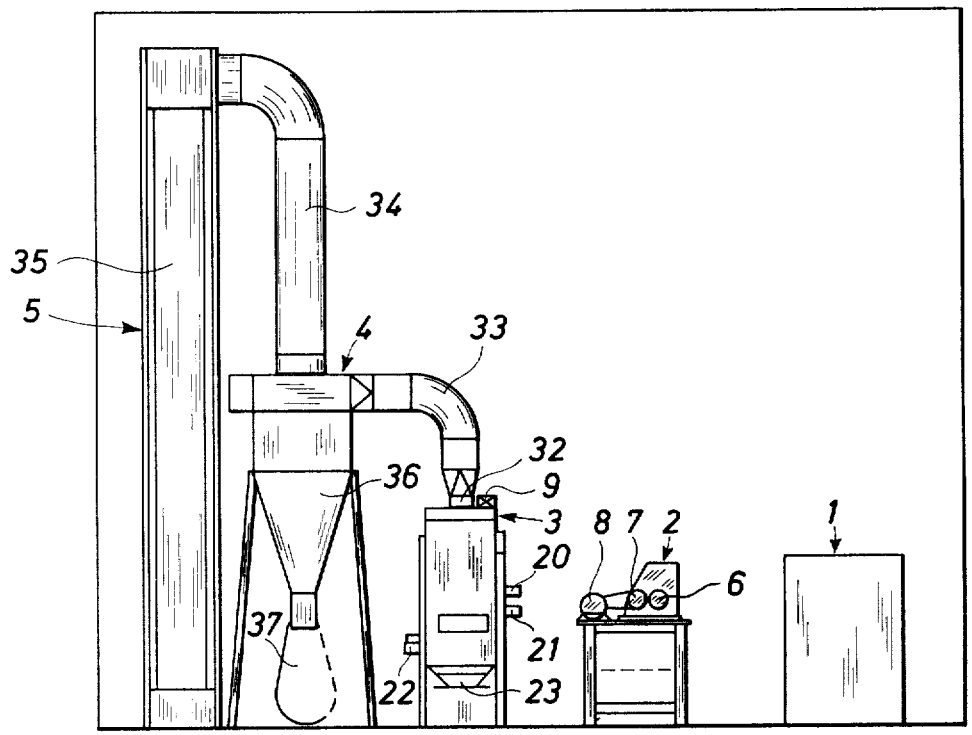

United States Patent [19]

Aagaard

[11] 3,960,329
[45] June 1, 1976

[54] METHOD AND APPARATUS FOR PURIFYING AND SEPARATING BEE GLUE

[76] Inventor: Karl Lund Aagaard, Vestergade 63, 3200 Helsinge, Denmark

[22] Filed: Dec. 16, 1974

[21] Appl. No.: 532,935

[30] Foreign Application Priority Data
Jan. 3, 1974   Luxembourg......................69108

[52] U.S. Cl.................................. 241/23; 241/24; 241/65
[51] Int. Cl.² .......................................... B02C 21/00
[58] Field of Search................ 241/DIG. 37, 23, 24, 241/65, 68

[56] References Cited
UNITED STATES PATENTS

| | | | |
|---|---|---|---|
| 2,276,333 | 3/1942 | Ovestrud............................. | 241/24 |
| 2,735,624 | 2/1956 | Beck............................ | 241/DIG. 37 |
| 2,836,368 | 5/1958 | McCoy........................ | 241/DIG. 37 |
| 3,527,414 | 9/1970 | Schorsch...................... | 241/DIG. 37 |
| 3,718,284 | 2/1973 | Richardson.................. | 241/DIG. 37 |

Primary Examiner—Granville Y. Custer, Jr.
Attorney, Agent, or Firm—Cushman, Darby & Cushman

[57] ABSTRACT

Method for purifying and separating bee glue (propolis) derived from beehives including the steps of firstly quick-freezing untreated propolis repeatedly at temperatures below −20°C, secondly crushing the thus treated propolis to smaller particles at a temperature below 10°C, thirdly separating said particles to a number of fractions according to size, the largest of said particles having a maximum diameter not much greater than 6 mm, and where fourthly said fractions containing most impurities are dissolved and filtered in a fluid filter for full utilization of all propolis present. Further an apparatus for performing said method comprising a deep-freezing apparatus, a crushing means, preferably a roller mill with rollers driven at different speeds, and a separating apparatus, preferably an aspirator with a number of screens, suction-ways, outlet channels and a permanent magnet at at least one outlet channel. and a cyclone placed in series with said aspirator.

5 Claims, 3 Drawing Figures

METHOD AND APPARATUS FOR PURIFYING AND SEPARATING BEE GLUE

The present invention relates to a method for purifying and separating bee glue (propolis) into various groups and an apparatus for performing said method.

It is well-known that the products of the bees and especially the products of Apis mellifera have many therapeutic properties so that these products can be used as medicaments. It is known to use propolis in dissolved form for wound treatment. German patent specification No. 1,037,651 discloses a method for extraction of a bacteriologically active substance from propolis. Also in Dansk Kemi 1973 (Danish Chemistry, 1973) in an article by cand. scient. Jens Hoiriis Nielsen entitled "Terapeutisk virksomme substanser i biharpikslimstoffet propolis" (Therapeutically Active Substances in the Bee Resin Gelatin Propolis) propolis is disclosed to have a germicidal effect.

It has been discovered that it is unnecessary to extract the individual antibiotics from the propolis, but that the substance in its natural form has a powerful curative effect on a plurality of different diseases such as chronic colitis, inflammation of the throat, rheumatic complaints, conjunctivitis etc. etc. as it appears from page 24 and the following in the book by K. Lund Aagaard with the title "Naturstoffet propolis - vejen til helbredelse" (The Natural Substance Propolis - the Road to Recovery) published by Mentor, Copenhagen, Denmark in 1973.

However, great difficulties are incurred in using the propolis scraped out of the beehives in natural form, as it contains many impurities, such as splinters, small metal pieces mostly iron or steel, bee wings and larvae and eggs of bee moths. To make the non-purified propolis useful as a medicament it is necessary to kill larvae and eggs, if any, and partly to purify it, so that the unadulterated product can be taken orally.

It is consequently the object of the present invention to provide a method for purifying and separating bee glue (propolis) from beehives into several components without changing in any way the chemical and physical composition of the pure substance.

The method is characterized by the fact that raw propolis is deep-frozen a number of times at intervals of a number of days; thereafter it is crushed and grated to grains with a maximum diameter of not over 6mm, thereafter the propolis grains with impurities are separated into fractions in a first apparatus; and a light remaining part is further divided into an additional number of fractions. By the repeated deep-freezing, larvae and eggs of wax moths and other existing living organisms, if any, are killed, while by crushing and grating with the subsequent division into fractions the greater part of the impurities can be sorted out; and by the last separation the last pollen-like granular remains of the propolis are ready for use.

The deep-freezing is undertaken in either a counter- or a conflow apparatus by quick freezing to a temperature of below −20°C with continuous treatment of the raw propolis. The freezing fluid used acts to kill any living organisms which, do not manage to become encysted to survive.

In certain cases it is advantageous that the deep-freezing is effectuated by storing the raw propolis in a deep-freezer at a temperature of below −20°C, as this is a cheaper method than the one stated above and is often sufficient to kill living organisms, if any.

Preferably, the raw propolis is crushed and grated to small grains in deep-frozen condition or in any case at temperatures not above 10°C in a crushing and grating means. By crushing and grating the raw propolis at the low temperature stated, the propolis which is glutinous and greasy at higher temperatures does not stick in the crushing and grating means; such sticking might cause time-consuming cleaning work. It is also easier to crush the raw propolis at the lower temperatures when it is rather friable and easy to crush.

After crushing and grating in the crushing means, the raw propolis is subjected to hardening and perhaps cooling, before the raw propolis is separated into groups, so that the propolis does not stick in the apparatus to be used for the dividing.

Preferably, the raw propolis is separated into a plurality, e.g. 7 fractions, in an aspirator by means of a number of screens and a suction means with a number of inlets for suction gas; either all, or only one fraction, is carried past a strong, permanent magnet. Thereby firstly, light particles such as dead bees, larvae of wax moths, voluminous wooden fragments are removed secondly ferruginous propolis pieces are removed from the remaining propolis grains which are simultaneously being sorted according to the size of the propolis grains.

It is further expedient that the lightest of the fractions from the aspirator is sucked into a cyclone, where this propolis fraction is further divided into two fractions. Hereby the possibility for utilizing also the smallest propolis particles is realized. In this connection one or both of the two lightest fractions can be collected in each its filter, so that the propolis can be regained by washing of the filters, when a suitable quantity of dust containing propolis has been collected in the filters.

Some of the fractions, i.e. the fractions which contain most impurities, can be dissolved in a solution liquid, e.g. alcohol and filtered in a fluid filter. A nature pure product is admittedly not obtained, but on the other hand, all propolis available is obtained, e.g. the propolis dust sitting on the insect remains is sorted out, as is iron or steel fragments.

For performing the above method according to the invention an apparatus is provided, which is characterized in that it comprises a deep freezing apparatus for deep freezing and hardening of the raw propolis, a crushing means for crushing and grating of the cold propolis to propolis grains and a separating apparatus for dividing raw propolis grains into a number of fractions, preferably seven fractions. This constitutes a simple and inexpensive apparatus, where the propolis can be purified and divided into groups suitable as merchandise. For the reasons stated above it is preferred that the deep-freezing system is a deep-freezing apparatus functioning according to either the counter- or conflow principle; as mentioned, in certain instances it can be expedient to use a deep-freezing system which consists of a conventional deep-freezer.

Preferably the crushing means is a rolling mill with knurled or fluted rollers, placed adjacent each other; by means of a motor, the rollers are driven at their respective speed of rotation for crushing the large and fairly large propolis lumps. Such a rolling mill has proved especially suitable for the crushing of the raw propolis lumps. Alternative crushing means, e.g. other mills, can be used.

The separating apparatus may consist of an aspirator, known per se, said aspirator may be equipped with a number of screens and a suction means with a number of suction ways through the aspirator and a number of outlet channels for the specific fractions. A permanent magnet is placed near or immediately near to each outlet channel. A very simple apparatus, results which has proved especially suitable for the present purposes, as it is modified to be capable of separating or removing ferruginous parts.

Preferably, a cyclone is placed in series with the separating apparatus for further dividing into two fractions. This series arrangement permits retaining the smallest propolis grains. This simple apparatus permits utilization of all the propolis present.

By the method and by the apparatus described above, purified propolis can be produced which is suitable for chewing and/or direct swallowing in e.g. the following catagories:

Coarse-grained and solid propolis on chewing which in connection with the enzymes, fluid of the saliva and body heat will result in evolution of a potent antibiotic after a few minutes. The propolis-saturated saliva is effective for wound treatment, burns, mouth cleaning etcetera.

The raw product in flour-form suitable for production of liniments, suppositories etcetera.

Figure 2:
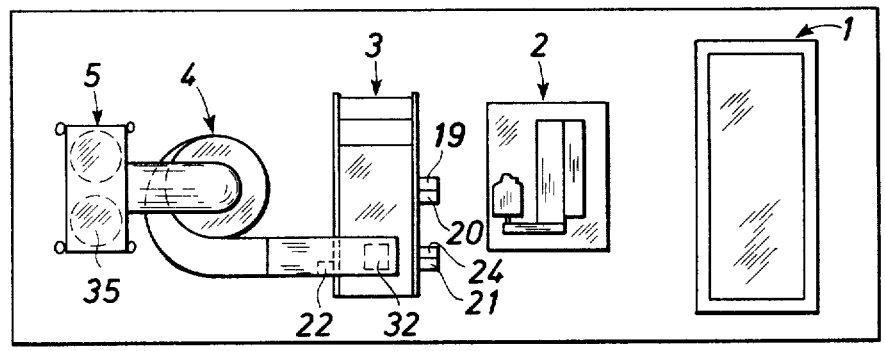
Figure 3:
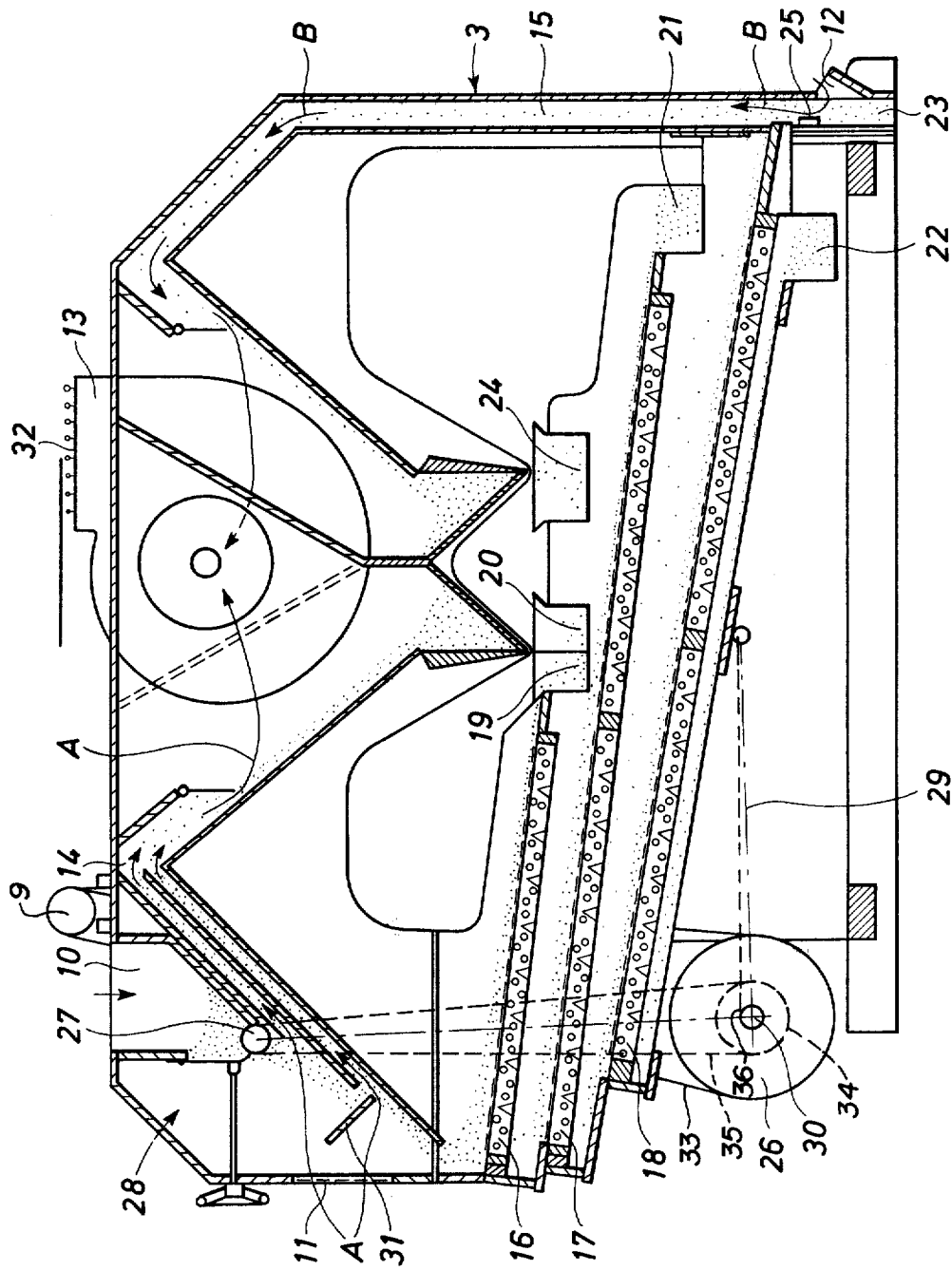

An example of a method and an example of an apparatus for cleaning and fractioning propolis appear from the following description with reference to the drawings, in which FIG. 1 is a side elevational view of a cleaning and separating apparatus, FIG. 2 is a top plan view of the apparatus, FIG. 3 is a sectional view of a barley cleaner.

An apparatus for cleaning and fractioning propolis comprises a deep freezing apparatus 1, a crushing means 2, an aspirator 3, a cyclone 4 and a filter 5.

The deep freezing apparatus 1 only shown diagrammatically may comprise a quick freezing means of the counter- or conflow type using e.g. liquid ammonia and a chamber for long-time storing of the deep frozen propolis at temperatures below −10°C, principally below −20°C and further an defreezing area and space for storage of the defrozen propolis at a temperature of above 20°C, principally of above 25°C. Preferably, the propolis substance (which is received from the apiculturist in big lumps and which at room temperature is greasy, stringy and sticky), is frozen and stored in deep-frozen condition for a long time, e.g. 2 days, so that larvae of waxmoths and other living organisms, if any are killed. After cold storage, the propolis is unfrozen and stored in a warm room for a long time to give viable eggs, if any, an opportunity to develop. The storage in the warm room is interrupted when notoriously all or essentially all eggs are developed, but before further egg-laying has taken place. Thereafter the propolis is refrozen. This process can be repeated according to requirement until it has been established that the propolis does not contain any viable organisms.

From the deep-freezing apparatus the frozen, consequently hard and friable propopolis substance is carried to the crushing means 2 at a temperature of about 0°C, where the propolis is pulverized and crushed so that propolis grains with a maximum extension of about 5 mm as well as floury propolis powder are formed. The crushing means 2 comprises expediently a couple of rollers 6, 7 driven by a motor 8. Parts of or the whole propolis portion can be crushed further in one or several succeeding roller pairs (which are not shown). To pulverize and grate the propolis substance further it is expedient that the rollers 6, 7 are fluted, knurled or are provided with engaged teeth with a mutual tightening, which secures that the propolis substance is grated or crushed to a suitable degree of fineness. To secure an effective grating, preferably the two rollers have different diameters, and, in the case of fluted or knurled rollers, also have different speeds of rotation. Preferably the preparation in the rollers takes place at an ambient temperature of about 0°C to maintain the friability which the propolis has at this temperature. Thus, propolis substance is easily crushed stated above, the propolis is sticky and greasy at room temperature. The rollers are not pasted down with greasy propolis substance by virtue of the freezing step. The freezing step, with respect to the rollers, obviates a laborious and long cleaning procedure.

The crushing means 2 can be any suitable crushing means, such as a pan grinder, a mill or any analogous crushing means. For the sake of clearness only a single kind of a crushing means is shown here.

From the crushing means the still cold crushed propolis is carried to the aspirator 3 for sorting or fractioning according to grain size. For the same reasons as stated above, preferably, this means 3 is kept at temperatures of about 0°C to facilitate the sorting or the fractioning. Obviously, the raw propolis carried to the aspirator is also to be at a suitably low temperature.

The aspirator comprises a driving means or a motor 9 for driving the aspirator (only shown in FIG. 1). The aspirator has an inlet 10 for conveying propolis grains and two air intakes 11, 12 for presuction and postsuction air respectively and a suction means 13 for producing the suction effect through the aspirator. The presuction air is carried through a divided presuction channel 14, past the incoming propolis and further on in the direction of the suction means 13, by the way indicated with arrows A, while the postsuction air is taken in at the air intake 12 and carried by the way indicated with arrows B through a postsuction channel 15 to the suction means 13. The aspirator comprises furthermore, a prescreen 16, a skimming screen 17 and a sand screen 18 all constructed as vibrating or ball screens, shown in FIG. 3. It is obvious that the different screens 16, 17, 18 have each a mesh adapted to the purpose.

Beyond this the aspirator comprises outlet channels for prescreen 19, for presuction 20, for skimming screen 21, for sand screen 22, for heavy articles 23 and for postsuction 24 and a permanent magnet 25 for removing the propolis grain with the content of iron or steel. It is obvious that also at the other channels permanent magnets (not shown) for collecting of propolis grains with a content of iron or steel may be placed. If it is not desired to provide the aspirator with several magnets it can be obtained only by omitting the screens above the sand screen 18 and by repetition of the operation that also the other fractions which are formed by passage through the aspirator pass the permanent magnet 25 for purifying from iron or steel pieces or grains containing iron or steel.

The aspirator is driven by the motor 9 via the belt 33 and a pulley 26, which via a pulley 34 and a belt 35 is connected with a feed roller 27 with grooves (not shown), which by co-operating with a regulating means 28 with a handle and a flexible regulating plate can regulate the influx of raw propolis and secure that no blocking or formation of cavities in the inlet 10 appears. The pulley 26 is placed at the end of a shaft 30, on which an eccentrically placed pin 36 is placed, said eccentrically placed pin 36 imparting a forward or backward movement to one or several rods 29 in order thereby to impart a vibrating movement to the individual screens.

The function of the aspirator is the following:

The propolis is carried to and poured into the inlet 10, from which it by means of the roller 27 is pulled down in suitable amounts and past the inlet opening for the divided presuction channel 14, whereby the first light particles are sucked upwards in the upper section of this channel. Thereafter the propolis falls down on a transverse board 31 and is guided past the other part of the presuction channel, whereby further light particles are sucked upwards in this channel. The particles sucked into the presuction channel pass through this, and the heaviest part of the presucked particles falls down into the outlet channel 20 for presuction, while the lightest particles are sucked upwards in the suction means and out through its orifice 32. The other grains fall down onto the prescreen 16, where the biggest particles are sorted out and fall down into the outlet channel 19 for the prescreen, while particles falling through the prescreen fall down onto the skimming screen 17. Here a sorting out takes place again and the article which cannot fall through the skimming screen passes through the outlet channel 21 for the skimming screen. On the sand screen 18 an analogous sorting out takes place the article falling through the sand screen 22 being sorted out on an outlet channel for the sand screen 22, whereas the heavy article falls down into the outlet channel 23 for heavy article. As this outlet channel 23 is connected to the postsuction channel 15, and as the grains as shown in the drawing fall down past the air intake for the postsuction air 12, this article will be purified further for remaining fine particles, if any, which are sucked into the postsuction channel 15, thereby either falling into the outlet channel 24 for postsuction or as far as the lightest part is concerned are sucked into the suction means 13 together with the light article coming from the presuction channel 14. As the grains in the outlet channel for heavy article further pass the permanent magnet 25, it is hereby secured that grains containing iron or steel, if any, are removed from the article. Thus a fractioning into seven fractions has taken place only by a single passage of grains through the aspirator, i.e. the material which runs out at the outlet channel for prescreen, for presuction for skimming screen, for sand screen, for heavy article, for postsuction respectively and at the permanent magnet.

It is obvious that a further fractioning may be effected according to requirement, perhaps by replacing the screens by other screens and repeated passage through the aspirator or by providing the aspirator with a larger number of screens for variation of the size of grains.

From the aspirator the lightest article is sucked through a tube 33 into a cyclone 4, where the lightest part of the light article sucked through the tube 33 is blown upwards through a channel 34 in order to fall down into a filter bag 35, where the rest of the propolis dust together with various light impurities are retained. The heavier part of the light article falls from the cyclone 4 through a funnel 36 and into a filter bag 37.

It has turned out that the heavy article falling down into the outlet channel 23 for heavy article constitutes a product which is sufficiently purified to be sold immediately as a medicament which can be taken in orally and chewed without inconveniences from impurities. On the contrary article falling into outlet channels for prescreen, for skimming screen and for sand screen respectively must pass once more, so that they pass the permanent magnet for taking out of particles with metal or steel pieces. Thereafter they constitute an expediently clean article.

The article falling into the outlet channels for presuction and postsuction respectively has proved expedient to be kneaded to suitable bars after having been softened at a reasonably high temperature, said bars may be used for combating of diseases, as e.g. paradentosis, by direct pressing onto the gingivia and between the teeth.

The article, which sticks on the permanent magnet and which falls down into the filter bags 35 and 37 respectively, can in an expedient way be used by being dissolved in alcohol or another solvent and thereafter being filtered through a liquid filter, so that the last impurities are removed, whereafter also this product can be used for certain forms of combating of diseases.

Result of Experiment

Out of 220 test persons 214 (97 per cent) report a positive result by treatment with propolis in one of the forms stated - coarse-granulated propolis, solid propolis, granulated propolis or propolis powder. Thus persons with the following diseases were cured (the number in the parenthesis states the number of persons):

It is obvious to an expert that also other separtion means than those stated above by way of example can be used, but the apparatus described here has proved the cheapest and most expedient. Thus a screening cylinder with gradually diminishing mesh may be used. Consequently, the above statement should in no way be considered limiting the present application, but only be regarded as an example of a method for fractioning and purifying of propolis.

I claim:

1. A method for purifying and separating bee glue (propolis) which is derived from beehives, comprising providing raw propolis and storing said propolis at temperatures below −10°C for a period of time sufficient to substantially destroy living organisms and larvae contained in said propolis; allowing the propolis to defrost at temperatures of about 20°C and maintaining said propolis at said temperature to allow the development of viable eggs of said larvae; refreezing said propolis for a period of time sufficient to destroy all viable organisms; crushing said propolis, wherein said propolis is maintained at a temperature of about 0° during said crushing, to produce grains of propolis having a maximum diameter of 6 mm; sorting and fractionating said crushed propolis, which is maintained at 0°C, according to grain size.

2. The method of claim 1, wherein said freezing is carried out in a counter-flow apparatus at a temperature of below −20°C by treatment with a freezing fluid.

3. The process of claim 1, wherein said freezing is carried out in a deep freezer at a temperature of below −20°C.

4. The process according to claim 1, wherein said propolis is sorted by means of an aspirator equipped with a suction means, said suction means provided with a series of screens for sorting said crushed propolis according to grain size; and wherein sorted propolis is subjected to a strong permanent magnet.

5. An apparatus for purifying and separating propolis, which has been frozen so as to be friable, including a crushing means for crushing and grating the frozen propolis to propolis grains; a separating apparatus which is an aspirator equipped with a number of screens and a suction means, which suction means communicate with said screens, said suction means provided with a number of outlets; and a permanent magnet adjacent to each of said outlets.

* * * * *